(12) United States Patent
Hayes et al.

(10) Patent No.: US 6,608,167 B1
(45) Date of Patent: Aug. 19, 2003

(54) BIS(2-HYDROXYETHYL ISOSORBIDE); PREPARATION, POLYMERS DERIVED THEREFROM, AND ENDUSES THEREBY

(75) Inventors: Richard Hayes, Brentwood, TN (US); Charles Brandenburg, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/108,023

(22) Filed: Mar. 26, 2002

(51) Int. Cl.[7] ............................................... C08G 63/02
(52) U.S. Cl. ....................... 528/271; 528/272; 528/298; 528/300; 528/302; 528/307; 528/308; 528/308.6; 525/437; 525/439; 525/440; 525/441; 525/444; 525/445
(58) Field of Search ............................ 528/271, 272, 528/298, 300, 302, 307, 308, 308.6; 525/437, 439, 440, 441, 444, 445

(56) References Cited

U.S. PATENT DOCUMENTS 6,063,464 A   5/2000   Charbonneau et al.

OTHER PUBLICATIONS

G. Fleche, et al., Starch/Starke. 38(1), pp. 26–30 (1986).

Ashton, et al., in Eur. J. Org. Chem., (5) pp. 995–1004 (1999).

El'perina, et al., in Izv. Akad. Nauk SSSR, Ser. Khim., (3) pp. 627–632 (1988).

Izv. Akad. Nauk SSSR, Ser, Khim., (3) pp. 632–637 (1988).

*Primary Examiner*—Samuel A. Acquah
(74) *Attorney, Agent, or Firm*—Inna Y. Belopolsky

(57) ABSTRACT

This invention provides a new, biomass-derived glycol, bis(2-hydroxyethyl)isosorbide, which is found to be a valuable monomer for a wide variety of polymeric materials.

4 Claims, No Drawings

BIS(2-HYDROXYETHYL ISOSORBIDE); PREPARATION, POLYMERS DERIVED THEREFROM, AND ENDUSES THEREBY

FIELD OF THE INVENTION

This invention provides a new, biomass-derived glycol, bis(2-hydroxyethyl)isosorbide, which is found to be a valuable monomer for a wide variety of polymeric materials.

TECHNICAL BACKGROUND OF THE INVENTION

There is a desire to utilize polymeric components ultimately derived from biomass. The diol 1,4:3,6-dianhydro-D-sorbitol, hereinafter referred to as isosorbide, is readily made from renewable resources, such as sugars and starches. For example, isosorbide can be made from D-glucose by hydrogenation followed by acid-catalyzed dehydration. The preparation of isosorbide is known within the literature in, for example, G. Fleche, et. al., *Starch/Starke*, 38(1), pp. 26–30 (1986). Isosorbide has the additional advantage of increasing the heat resistance of a polyester into which it is incorporated by raising its glass transition temperature (Tg).

Charbonneau, et. al., in U.S. Pat. No. 6,063,464, describe a process to produce polyesters which incorporate isosorbide, that have an inherent viscosity of at least 0.35 dL/g when measured as a 1% (weight/volume) solution of the polyester in o-chlorophenol at a temperature of 25° C. They generally teach the use of aromatic and alicyclic diacids. A shortcoming found in this disclosure was the low incorporation rate of the isosorbide monomer. Of the 16 preparative examples included within this disclosure where the percentage of incorporated isosorbide into the polymer could be assessed, the incorporation level of added isosorbide monomer into the as produced polymer ranged from 12 to 70 percent. The average incorporation rate of added isosorbide monomer into the polymer was disclosed to be 48 percent. As one skilled in the art would appreciate, this inefficiency of isosorbide monomer incorporation into the polymer leads to complex glycol recovery and separation processes.

The present invention overcomes this shortcoming and provides chemically modified isosorbide derivatives which allow for essentially complete incorporation into high molecular weight polymers derived therefrom. The essentially complete incorporation of isosorbide allows avoidance of complex glycol recovery and separation processes.

The present invention provides valuable polymeric materials, such as polyesters, polyamide esters, polyurethanes and polycarbonates which incorporate said chemically modified isosorbide derivatives.

One aspect of the present invention includes 1,4:3,6-dianhydro-2,5-bis-O-(2-hydroxyethyl)-D-sorbitol, hereinafter referred to as bis(2-hydroxyethyl)isosorbide. Heretofore, bis(2-hydroxyethyl)isosorbide has not been reported within the art. Similar derivatives of D-mannitol have been reported. 1,4:3,6-dianhydro-2,5-bis-O-(2-hydroxyethyl)-D-mannitol, hereinafter referred to as bis(2-hydroxyethyl) mannitol, has been prepared as an intermediate in the preparation of crown ethers. For example, Ashton, et. al., in *Eur. J. Org. Chem.*, (5), pp. 995–1004 (1999), reported the preparation of bis(hydroxyethyl)mannitol for use in the preparation of crown ethers. El'perina, et. al., in *Izv. Akad. Nauk SSSR, Ser. Khim.*, (3), pp. 627–632 (1988) and in *Izv. Akad. Nauk SSSR, Ser. Khim.*, (3), pp. 632–637 (1988), prepared bis(2-hydroxyethyl)mannitol through base-catalyzed alkylation of mannitol with 2-(2-bromoethoxy) tetrahydropyran, followed by deprotection of the alcohol function. This material was further utilized in the production of crown ethers. As one skilled in the art would appreciate, the stereo- and regiochemistry of said bis(2-hydroxyethyl) mannitol, which makes it useful as a precursor for crown ethers, would lead to significant cyclic oligomer formation in the production of the valuable polymeric materials described herein. Significant cyclic oligomer levels in polymeric materials are not desirable for most end uses described herein.

SUMMARY OF THE INVENTION

One aspect of the present invention includes a new composition of matter termed bis(2-hydroxyethyl) isosorbide. Bis(2-hydroxyethyl)isosorbide may be prepared through chemical modification of isosorbide. Polymeric materials derived from bis(2-hydroxyethyl)isosorbide, such as polyesters, polyamide esters, polyurethanes, polycarbonates, and the like, are useful in a wide variety of shaped articles, such as films, sheets, containers, fibers, molded parts, coatings, foamed articles, and the like.

A further aspect of the present invention includes polyesters which incorporate bis(2-hydroxyethyl)isosorbide. Said polyesters which incorporate bis(2-hydroxyethyl) isosorbide are comprised essentially of 45.0 to 50.0 mole percent dicarboxylic acid component, 50.0–0.1 mole percent bis(2-hydroxyethyl)isosorbide, 0 to 49.9 mole percent of a glycol component, and 0 to 5.0 mole percent of a polyfunctional branching agent. Said polyesters which incorporate bis(2-hydroxyethyl)isosorbide of the present invention are found to have a greater monomer incorporation rate than the isosorbide polyesters of the art.

A further aspect of the present invention includes polyurethanes which incorporate bis(2-hydroxyethyl)isosorbide. Said polyurethanes which incorporate bis(2-hydroxyethyl) isosorbide are comprised essentially of 45.0 to 50.0 mole percent of a polyisocyanate component, 50.0 to 0.1 mole percent of bis(2-hydroxyethyl)isosorbide and/or a polyester polyol which contains bis(2-hydroxyethyl)isosorbide, and 0 to 49.9 mole percent of a glycol component.

A further aspect of the present invention includes shaped articles produced from polymeric materials which incorporate bis(2-hydroxyethyl)isosorbide. Said polymeric materials which incorporate bis(2-hydroxyethyl)isosorbide may be selected from the group consisting of polyesters, polyamide esters, polyurethanes, polyether sulfones, polyether ketones, polycarbonates, and polycarbonate esters. Said shaped articles produced from the polymeric materials which incorporate bis(2-hydroxyethyl)isosorbide of the present invention may include film, sheets, fiber, melt blown containers, molded parts, such as cutlery, foamed parts, polymeric melt extrusion coatings onto substrates, polymeric solution coatings onto substrates and the like.

DETAILED DESCRIPTION OF THE INVENTION

Preparation of bis(2-hydroxyethyl)isosorbide

The bis(2-hydroxyethyl)isosorbide of the present invention may be readily prepared from isosorbide, which is derived from renewable resources, such as sugars and starches, as described above. For example, isosorbide may be modified with ethylene oxide, ethylene carbonate and the like, to produce bis(2-hydroxyethyl)isosorbide.

The conversion of alcohols to 2-hydroxyethyl ethers is known within the art. Any known method in the art may be used to convert isosorbide to bis(2-hydroxyethyl)isosorbide.

Ethylene Oxide

For example, ethylene oxide has been used in the production of 2-hydroxyethyl ethers from alcohols. Typically such a process is performed by heating the ethylene oxide, the alcohol and a catalyst system together, followed by recovery and purification of the resultant 2-hydroxyethyl ether product. The reaction may be performed with an inert solvent. Catalyst systems which have found use in such processes include; acids, bases, ammonia, urea, alkali metal hydroxides, alkali metal phenates, potassium hydroxide, alkali metal bases, organoaluminum zinc compounds, nitrogen containing catalysts, calcium acetates, strontium acetates, barium acetates, aluminum trifluoride, trialkyl aluminum, mixtures of boron trifluoride and trialkyl phosphoric compounds, zinc dialkyl materials, mixtures of boron trifluoride with metal alkyls or metal alkoxides, mixtures of silicon tetrafluoride with metal alkyls or metal alkoxides, mixtures of an alkali metal borohydride and an alkali metal hydroxide. Representative art which describes the preparation of 2-hydroxyethyl ethers from alcohols would include; U.S. Pat. Nos. 2,716,137, 2,852,566, 2,879,220, 3,350,462, 3,354,227, 3,364,267, 3,395,185, 3,525,773, 3,597,502, 3,642,911, 3,644,534, 3,682,849, 3,719,636, 3,910,878, 3,969,417, 4,098,818, 4,210,764, 4,223,164, 4,239,917, 4,254,287, 4,282,387, 4,302,613, 4,306,093, 4,453,022, 4,453,023, 4,483,941, 4,533,759, 4,754,075, 4,775,653, 4,820,673, 4,886,917, 4,892,977, 4,902,658, 5,608,116 British Patent No. 1,399,966, British Patent No. 1,462,133, British Patent No. 1,462,134, European Patent Application No. A0095562, European Patent Application No. 339426, French Patent No. 1,365,945, German Patent No. 2406293, Japanese Patent No. 50017976, Japanese Patent No. 50000654, Japanese Patent No. 49033183, Japanese Patent No. 62289537, Japanese Patent No. 52003923, Japanese Patent No. 52051307, Japanese Patent No. 51059809 and references cited therein. These preparative references and the references cited therein are herein incorporated by reference into the present invention.

Catalysts that may be used with the ethylene oxide include acids, bases, ammonia, urea, alkali metal hydroxides, alkali metal phenates, potassium hydroxide, alkali metal bases, organoaluminum zinc compounds, nitrogen containing catalysts, calcium acetates, strontium acetates, barium acetates, aluminum trifluoride, trialkyl aluminum, mixtures of boron trifluoride and trialkyl phosphoric compounds, zinc dialkyl materials, mixtures of boron trifluoride with metal alkyls or metal alkoxides, mixtures of silicon tetrafluoride with metal alkyls or metal alkoxides, mixtures of an alkali metal borohydride and an alkali metal hydroxide, and the like and mixtures thereof. These are generally known in the art and a skilled practitioner may readily select the specific catalyst or combination or sequence of catalysts used. The preferred catalyst and preferred conditions differ depending on, for example, the type and scale of reactor to be used.

Ethylene Carbonate

Ethylene carbonate has been used in the conversion of alcohols to 2-hydroxyethyl ethers. Typically this operation is performed by heating the alcohol, ethylene carbonate and certain catalyst systems together, followed by recovery of the resultant 2-hydroxyethyl ether product. The process may be carried out with an inert solvent. Generally, the catalyst systems may be composed of acids, bases, alkali salts of phenols, phosphonium materials, potassium carbonate, alkali metal hydrides, alkali metal hydroxides, inorganic halide salts, triorganophosphine compounds, potassium iodide, imidazole, sodium stannate, potassium fluoride, mixed metal oxide. Representative art would include U.S. Pat. Nos. 2,448,767, 2,967,892, 2,987,555, 3,283,030, 3,967,892, 4,261,922, 4,310,706, 4,310,707, 4,310,708, 4,341,905, 5,059,723, 5,104,987, 5,157,159, 5,679,871, 5,998,568, Japanese Patent No. 03052838, Japanese Patent No. 50004012 and references cited therein. Dow Chemical U.S.A., Experimental Ethylene carbonate XAS-1666.00L Product Bulletin (1982), pp. 4–9, discloses hydroxyethylation reactions in which ethylene carbonate reacts with compounds containing active hydrogen, such as alcohols, to give hydroxyethyl derivatives. The reactions are carried out at temperatures between 100° C. to 200° C. in the presence of metal salts such as potassium carbonate. Carbon dioxide is the principle byproduct. It is stated that ethylene carbonate yields, in most cases, the mono-ethylene oxide insertion product. Texaco Chemical Company, TEXACAR.RTM. Ethylene and Propylene Carbonates Product Bulletin (1987), pp. 23–24, describes hydroxyalkylation reactions in which ethylene carbonate react with compounds which contain an active hydrogen, such as alcohols, to give the corresponding hydroxyethyl derivatives. The reactions are run between 100 and 200° C. employing a basic catalyst, such as potassium carbonate at a 0.5 weight percent level. These preparative references and the references cited therein are hereby incorporated by reference into the present invention.

Catalysts that may be used with the ethylene carbonate include, for example, acids, bases, alkali salts of phenols, phosphonium materials, potassium carbonate, alkali metal hydrides, alkali metal hydroxides, inorganic halide salts, triorganophosphine compounds, potassium iodide, imidazole, sodium stannate, potassium fluoride, mixed metal oxide, and the like and mixtures thereof. These are generally known in the art and a skilled practitioner may readily select the specific catalyst or combination or sequence of catalysts used. The preferred catalyst and preferred conditions differ depending on, for example, the type and scale of reactor to be used.

Chemical Modification

In the chemical modification process, the isosorbide and the ethylene oxide or the ethylene carbonate are combined and are heated gradually with mixing with a catalyst or a catalyst mixture to a temperature in the range of 50 to about 300° C., preferably between 75 and 200° C. Typically a stoichiometric excess of ethylene carbonate will be employed. Optionally, a solvent inert under the reaction conditions, such as a hydrocarbon, may be employed. The exact conditions and catalysts used will depend on the exact nature of the reactor to be employed. The catalyst may be included initially with the reactants and/or may be added one or more times to the mixture as it is heated. The catalyst used may be modified as the reaction proceeds. The heating and stirring are continued for a sufficient time and a sufficient temperature to yield a significant conversion of isosorbide to bis(hydroxyethyl)isosorbide.

Purification of bis(2-hydroxyethyl)isosorbide

The resulting bis(2-hydroxyethyl)isosorbide product may be purified by any method known within the art, for example, by distillation. As is known within the art, hydroxyethylation processes with ethylene oxide or ethylene carbonate generally lead to a mixture of products. Said mixture typically is the result of the initially formed bis(2-hydroxyethyl)isosorbide product further reacting with additional ethylene carbonate to form higher hydroxy terminated polyethers. Formation of such higher polyethers may be controlled by the amount of added ethylene carbonate, the exact nature of the catalyst system, and the reaction conditions. While it is most preferred that the bis(2-hydroxyethyl)

isosorbide to be used in the preparation of the polymeric materials described below be essentially pure, it is contemplated that bis(2-hydroxyethyl)isosorbide may include said higher hydroxy terminated polyethers derived from additional hydroxyethylation reactions between ethylene carbonate and the as formed products. It is preferred that such impurities be below 10 weight percent of the bis(2-hydroxyethyl)isosorbide product.

A wide variety of other preparative methods for the preparation of 2-hydroxyethyl ethers have been reported within the art. For example, Shibatani, et. al., in Japanese Patent 53098917, describe the conversion of alcohols to 2-hydroxyethyl ethers by reacting the alcohols with formaldehyde, hydrogen, and carbon monoxide in the presence of oxo catalysts. Any known preparative method to produce 2-hydroxyethyl ethers may find use in the present invention. Uses of bis(2-hydroxyethyl)isosorbide:

Uses of bis(2-hydroxyethyl)isosorbide

Bis(2-hydroxyethyl)isosorbide will find many valuable uses in the art. Bis(2-hydroxyethyl)isosorbide may be chemically modified to form, for example bisacrylate esters or bis vinyl ethers, which will find use in photochemical or thermal cured vinyl resin compositions. Alternatively, bis (2-hydroxyethyl)isosorbide may be reacted with epichlorohydrin and base to form bis(glycidyl ether) adducts which may serve in epoxy resins. For example, bis(2-hydroxyethyl)isosorbide will find use as a monomer in polymeric compositions, such as polyesters, polyamide esters, polycarbonates, polycarbonate esters, polyurethanes, polyether sulfones, polyether ketones, polyether ether ketones, and the like.

Polyesters

One further aspect of the present invention includes polyesters which incorporate bis(2-hydroxyethyl) isosorbide. Said polyesters with bis(2-hydroxyethyl) isosorbide comonomer are comprised essentially of:

(a) 45.0 to 50.0 mole percent of a dicarboxylic acid component, (b) 50.0 to 0.1 mole percent of bis(2-hydroxyethyl) isosorbide, (c) 0 to 49.9 mole percent of at least one additional glycol component, and (d) 0 to 5.0 mole percent of at least one polyfunctional branching agent.

Said dicarboxylic acid component is meant to include unsubstituted and substituted aromatic, aliphatic, unsaturated, and acyclic dicarboxylic acids and the lower alkyl esters of aromatic, aliphatic, unsaturated, and acyclic dicarboxylic acids having from 8 carbons to 36 carbons. Specific examples of the desirable dicarboxylic acid component include terephthalic acid, dimethyl terephthalate, isophthalic acid, dimethyl isophthalate, 2,6-napthalene dicarboxylic acid, dimethyl-2,6-naphthalate, 2,7-naphthalenedicarboxylic acid, dimethyl-2,7-naphthalate, 3,4'-diphenyl ether dicarboxylic acid, dimethyl-3,4'diphenyl ether dicarboxylate, 4,4'-diphenyl ether dicarboxylic acid, dimethyl4,4'-diphenyl ether dicarboxylate, 3,4'-diphenyl sulfide dicarboxylic acid, dimethyl-3,4'-diphenyl sulfide dicarboxylate, 4,4'-diphenyl sulfide dicarboxylic acid, dimethyl4,4'-diphenyl sulfide dicarboxylate, 3,4'-diphenyl sulfone dicarboxylic acid, dimethyl-3,4'-diphenyl sulfone dicarboxylate, 4,4'-diphenyl sulfone dicarboxylic acid, dimethyl4,4'-diphenyl sulfone dicarboxylate, 3,4'-benzophenonedicarboxylic acid, dimethyl-3,4'-benzophenonedicarboxylate, 4,4'-benzophenonedicarboxylic acid, dimethyl4,4'-benzophenonedicarboxylate, 1,4-naphthalene dicarboxylic acid, dimethyl-1,4-naphthalate, 4,4'-methylene bis(benzoic acid), dimethyl-4,4'-methylenebis(benzoate), and the like and mixtures derived therefrom. Preferably, the aromatic dicarboxylic acid component is derived from terephthalic acid, dimethyl terephthalate, isophthalic acid, dimethyl isophthalate, 2,6-naphthalene dicarboxylic acid, dimethyl-2,6-naphthalate, metal salts of 5-sulfo-dimethylisophthalate, oxalic acid, dimethyl oxalate, malonic acid, dimethyl malonate, succinic acid, dimethyl succinate, methylsuccinic acid, glutaric acid, dimethyl glutarate, 2-methylglutaric acid, 3-methylglutaric acid, adipic acid, dimethyl adipate, 3-methyladipic acid, 2,2,5,5-tetramethylhexanedioic acid, pimelic acid, suberic acid, azelaic acid, dimethyl azelate, sebacic acid, 1,1 1-undecanedicarboxylic acid, 1,10-decanedicarboxylic acid, undecanedioic acid, 1,12-dodecanedicarboxylic acid, hexadecanedioic acid, docosanedioic acid, tetracosanedioic acid, dimer acid, 1,4-cyclohexanedicarboxylic acid, dimethyl-1,4-cyclohexanedicarboxylate, 1,3-cyclohexanedicarboxylic acid, dimethyl-1,3-cyclohexanedicarboxylate, 1,1-cyclohexanediacetic acid, fumaric acid, maleic anhydride, maleic acid, hexahydrophthalic acid, phthalic acid, and the like and mixtures derived therefrom. These examples should not be considered limiting. Essentially any dicarboxylic acid known within the art may find utility within the present invention.

Said other glycol component is meant to include unsubstituted, substituted, straight chain, branched, cyclic aliphatic, aliphatic-aromatic or aromatic diols having from 2 carbon atoms to 36 carbon atoms and poly(alkylene ether) glycols with molecular weights between about 250 to 4,000. Specific examples of the desirable other glycol component include ethylene glycol, 1,3-propanediol, 1,2-propanediol, 1,2-butanediol, 1,3-butanediol, 1,3-2-methylpropanediol, neopentyl glycol, 1,4-butanediol, 1,3-hexanediol, 1,6-hexanediol, 2-ethyl-2-methyl-1,3-propanediol, 1,8-octanediol, 1,10-decanediol, 1,12-dodecanediol, 1,14-tetradecanediol, 1,16-hexadecanediol, dimer diol, 4,8-bis (hydroxymethyl)-tricyclo[5.2.1.0/2.6]decane, 1,4-cyclohexanedimethanol, di(ethylene glycol), tri(ethylene glycol), poly(ethylene ether) glycols, poly(butylene ether) glycols and the like and mixtures derived therefrom. These examples should not be interpreted as limiting. Essentially any other glycol known within the art may find use within the present invention.

Said optional polyfunctional branching agent is meant to include any material with three or more carboxylic acid functions, hydroxy functions or a mixture thereof. Specific examples of the desirable polyfunctional branching agent component include 1,2,4-benzenetricarboxylic acid, (trimellitic acid), trimethyl-1,2,4-benzenetricarboxylate, 1,2,4-benzenetricarboxylic anhydride, (trimellitic anhydride), 1,3,5-benzenetricarboxylic acid, 1,2,4,5-benzenetetracarboxylic acid, (pyromellitic acid), 1,2,4,5-benzenetetracarboxylic dianhydride, (pyromellitic anhydride), 3,3',4,4'-benzophenonetetracarboxylic dianhydride, 1,4,5,8-naphthalenetetracarboxylic dianhydride, citric acid, tetrahydrofuran-2,3,4,5-tetracarboxylic acid, 1,3,5-cyclohexanetricarboxylic acid, pentaerythritol, 2-(hydroxymethyl)-1,3-propanediol, 2,2-bis (hydroxymethyl)propionic acid, trimer acid, and the like and mixtures therefrom. This should not be considered limiting. Essentially any polyfunctional material which includes three or more carboxylic acid or hydroxyl functions may find use within the present invention. Said polyfunctional branching agent may be included when higher resin melt viscosity is desired for specific end uses. Examples of said end uses may include melt extrusion coatings, melt blown films or containers, foam and the like.

To give the desired physical properties for many end uses, the polyesters which incorporate bis(2-hydroxyethyl) isosorbide of the present invention need to have an inherent viscosity, which is an indicator of molecular weight, of at least equal to or greater than 0. 15. More desirably, the inherent viscosity, (IV), of polyesters which include bis(2-hydroxyethyl)isosorbide will be at least equal to 0.35 dL/g, as measured on a 0.5 percent (weight/volume) solution of the copolyester in a 50:50 (weight) solution of trifluoroacetic acid:dichloromethane solvent system at room temperature. These inherent viscosities will be sufficient for some applications. Higher inherent viscosities are desirable for many other applications, such as films, bottles, sheet, molding resin and the like. The polymerization conditions may be adjusted to obtain the desired inherent viscosities up to at least about 0.5 and desirably higher than 0.65 dL/g. Further processing of the polyester may achieve inherent viscosities of 0.7, 0.8, 0.9, 1.0, 1.5, 2.0 dL/g and even higher.

The molecular weight is normally not measured directly. Instead, the inherent viscosity of the polymer in solution or the melt viscosity is used as an indicator of molecular weight. The inherent viscosities are an indicator of molecular weight for comparisons of samples within a polymer family, such as poly(ethylene terephthalate), poly(butylene terephthalate), etc., and are used as the indicator of molecular weight herein.

Alternatively, certain polyester end uses prefer relatively low molecular weight materials. For example, polyester polyols are used in the preparation of, for example, polyurethanes and polycarbonate esters. The polyester polyols of the present invention which incorporate bis(2-hydroxyethyl) isosorbide may have molecular weights in the range between 500 and 10,000.

The polyesters of the present invention may be prepared by conventional polycondensation techniques. A review reference on polyesters and their manufacture is Anthony J. East, Michael Golden, and Subhash Makhija, in Encyclopedia of Chemical Technology, vol. 19, fourth edition, Executive Editor, Jacqueline I. Kroschwitz, Editor, Mary Howe-Grant, pp. 609–653 (1996), which is hereby incorporated by reference in the present invention. The product compositions may vary somewhat based on the method of preparation used, particularly in the amount of diol that is present within the polymer. These methods include the reaction of the diol monomers with the acid chlorides. For example, acid chlorides of the dicarboxylic acid component may be combined with the bis(2-hydroxyethyl)isosorbide and the other glycol component in a solvent, such as toluene, in the presence of a base, such as pyridine, which neutralizes the hydrochloric acid as it is produced. Such procedures are known. See, for example, R. Storbeck, et. al., in *J. Appl. Polymer Science,* Vol. 59, pp.1199–1202 (1996). Other well known variations using acids chlorides may also be used, such as the interfacial polymerization method, or the monomers may simply be stirred together while heating.

When an isosorbide-containing polyester is made using acid chlorides, the ratio of the monomer units in the product polymer is about the same as the ratio of reacting monomers. Therefore, the ratio of monomers charged to the reactor is about the same as the desired ratio in the product. A stoichiometric equivalent of the diol components and the diacid components generally will be used to obtain a high molecular weight polymer.

Polyester Preparation

Preferably, the polyesters which incorporate bis(2-hydroxyethyl)isosorbide of the present invention will be produced through a melt polymerization method. In the melt polymerization method, the dicarboxylic acid component, (either as acids, esters, or mixtures thereof), the bis(2-hydroxyethyl)isosorbide, the other glycol component and optionally the polyfunctional branching agent, are combined in the presence of a catalyst to a high enough temperature that the monomers combine to form esters and diesters, then oligomers, and finally polymers. The polymeric product at the end of the polymerization process is a molten product. Generally, the other diol component is volatile and distills from the reactor as the polymerization proceeds. Such procedures are known. See, for example, U.S. Pat. Nos. 3,563,942, 3,948,859, 4,094,721, 4,104,262, 4,166,895, 4,252,940, 4,390,687, 4,419,507, 4,585,687, 5,053,482, 5,292,783, 5,446,079, 5,480,962, and 6,063,464 and the references cited therein, which are herein incorporated by reference.

The melt process conditions of the present invention, particularly the amounts of monomers used, depend on the polymer composition that is desired. The amount of bis(2-hydroxyethyl)isosorbide, other glycol component, dicarboxylic acid component, and branching agent are desirably chosen so that the final polymeric product contains the desired amounts of the various monomer units, desirably with equimolar amounts of monomer units derived from the respective diol and diacid components. Because of the volatility of some of the monomers, especially some of the other glycol components, and depending on such variables as whether the reactor is sealed, (i.e., is under pressure), the polymerization temperature ramp rate, and the efficiency of the distillation columns used in synthesizing the polymer, some of the monomers may need to be included in excess at the beginning of the polymerization reaction and removed by distillation as the reaction proceeds. This is particularly true of the other glycol component.

The exact amount of monomers to be charged to a particular reactor is readily determined by a skilled practitioner, but often will be in the ranges below. Excesses of the diacid, diol, and bis(2-hydroxyethyl)isosorbide are often desirably charged, and the excess diacid, diol and bis(2-hydroxyethyl)isosorbide is desirably removed by distillation or other means of evaporation as the polymerization reaction proceeds. The other glycol component is desirably charged at a level 0 to 100 percent greater than the desired incorporation level in the final product. For examples of the other glycol component which are volatile under the polymerization conditions, such as ethylene glycol, 1,3-propanediol, or 1,4-butanediol, 30 to 100 percent excesses are desirably charged. For less volatile examples of the other glycol component, such as dimer diol, no excesses need be desirably charged.

The amount of monomers varies widely because of the wide variation in the monomer loss during polymerization, depending on the efficiency of distillation columns and other kinds of recovery and recycle systems and the like, and are only an approximation. Exact amounts of monomers that are charged to a specific reactor to achieve a specific composition are readily determined by a skilled practitioner.

In the polymerization process, the monomers are combined, and are heated gradually with mixing with a catalyst or catalyst mixture to a temperature in the range of 200° C. to about 300° C., desirably 250° C. to 295° C. The exact conditions and the catalysts depend on whether the diacids are polymerized as true acids or as dimethyl esters. The catalyst may be included initially with the reactants, and/or may be added one or more times to the mixture as it is heated. The catalyst used may be modified as the reaction proceeds. The heating and stirring are continued for a sufficient time and to a sufficient temperature, generally with removal by distillation of excess reactants, to yield a molten polymer having a high enough molecular weight to be suitable for making fabricated products.

Catalysts that may be used include salts of Li, Ca, Mg, Mn, Zn, Pb, Sb, Sn, Ge, and Ti, such as acetate salts and oxides, including glycol adducts, and Ti alkoxides. These catalysts are generally known in the art, and a skilled practitioner may readily select the specific catalyst or combination or sequence of catalysts used. The preferred catalyst and preferred conditions differ depending on, for example, whether the diacid monomer is polymerized as the free diacid or as a dimethyl ester and the exact chemical identity of the other glycol component.

The monomer composition of the polymer is chosen for specific uses and for specific sets of properties. For uses where a partially crystalline polymer is desired, as for example food and beverage containers, specifically, such as hot fill or cold fill bottles, fibers, and films, the polymer will generally have a monomer composition which allows for some crystallinity in the final polymer product.

For applications where it is desirable to have an amorphous polymer, for example, transparent optical articles or solvent soluble copolyesters, the amount of bis(2-hydroxyethyl)isosorbide moiety is generally greater than 2.0 mole percent. As one skilled in the art will appreciate, the exact thermal properties observed will be a complex function of the exact chemical identity and level of each component utilized in the copolyester composition.

Polymers can be made by the melt condensation process above having adequate inherent viscosity for many applications. Solid state polymerization may be used to achieve even higher inherent viscosities (molecular weights).

Crystallinity

The product made by melt polymerization, after extruding, cooling and pelletizing, may be essentially non-crystalline. Noncrystalline material can be made semicrystalline by heating it to a temperature above the glass transition temperature for an extended period of time. This induces crystallization so that the product can then be heated to a higher temperature to raise the molecular weight.

The polymer may also be crystallized prior to solid state polymerization by treatment with a relatively poor solvent for polyesters which induces crystallization. Such solvents reduce the glass transition temperature (Tg) allowing for crystallization. Solvent induced crystallization is known for polyesters and is described in U.S. Pat. Nos. 5,164,478 and 3,684,766, which are incorporated herein by reference.

The semicrystalline polymer is subjected to solid state polymerization by placing the pelletized or pulverized polymer into a stream of an inert gas, usually nitrogen, or under a vacuum of 1 Torr, at an elevated temperature, but below the melting temperature of the polymer for an extended period of time.

Some of the above described polyesters which incorporate bis(2-hydroxyethyl)isosorbide are found to be t soluble in common, non-halogenated, polar solvents. Examples of said non-halogenated, polar solvents include tetrahydrofuran, dimethyl acetamide, dimethyl formamide, N-methylpyrollidone, dimethylsulfoxide, and the like. Tetrahydrofuran is preferred. Certain examples of the polyesters which incorporate bis(2-hydroxyethyl)isosorbide of the current invention are found to be readily soluble in said solvents and the resulting polymer solutions are found to provide clear films.

Additives

It is understood that the polyesters which incorporate bis(2-hydroxyethyl)isosorbide of the present invention may be used with additives known within the art. Such additives may include thermal stabilizers, for example, phenolic antioxidants, secondary thermal stabilizers, for example, thioethers and phosphites, UV absorbers, for example benzophenone- and benzotriazole-derivatives, UV stabilizers, for example, hindered amine light stabilizers, (HALS), and the like. Said additives may further include plasticizers, processing aides, flow enhancing additives, lubricants, pigments, flame retardants, impact modifiers, nucleating agents to increase crystallinity, antiblocking agents such as silica and the like. In addition, the compositions of the present invention may be filled with, for example, wood flour, gypsum, wollastonite, chalk, kaolin, clay, silicon oxide, calcium terephthalate, aluminum oxide, titanium oxide, calcium phosphate, lithium fluoride, cellulose, starch, chemically modified starch, thermoplastic starch, calcium carbonate, reinforcing agents, such as glass, and the like. The compositions of the present invention may also find use as a component of a polymer blend with other polymers, such as cellulose ethers, thermoplastic starch, poly(vinyl alcohol), other polyesters, polycarbonates, nylons, polyamides, polyolefins, polyolefin elastomers, and the like. This should not be considered limiting. Essentially any additive and filler of the art may find use in the polyesters which incorporate bis(2-hydroxyethyl)isosorbide of the present invention.

Biodegradability

Some of the polyester compositions of the present invention which incorporate bis(2-hydroxyethyl)isosorbide will be found to be biodegradable, as determined through the below mentioned ISO 14855 composting method. Preferably, said biodegradable copolyester of the present invention which incorporate bis(2-hydroxyethyl)isosorbide will contain, at least as a portion of the dicarboxylic acid component, aliphatic dicarboxylic acids.

The inadequate treatment of municipal solid waste which is being put in landfills and the increasing addition of nondegradable materials, including plastics, to municipal solid waste streams are combining to drastically reduce the number of landfills available and to increase the costs of municipal solid waste disposal. While recycling of reusable components of the waste stream is desirable in many instances, the costs of recycling and the infrastructure required to recycle materials is sometimes prohibitive. In addition, there are some products which do not easily fit into the framework of recycling. The composting of non-recyclable solid waste is a recognized and growing method to reduce solid waste volume for landfilling and/or making a useful product from the waste to improve the fertility of fields and gardens. One of the limitations to marketing such compost is the visible contamination by undegraded plastic, such as film or fiber fragments.

It is desired to provide components which are useful in disposable products and which are degraded into less contaminating forms under the conditions typically existing in waste composting processes. These conditions may involve temperatures no higher than 70 degrees C., and averaging in the 55–60 degrees C. range, humid conditions as high as 100 percent relative humidity, and exposure times which range from weeks to months. It is further desirable to provide disposable components which will not only degrade aerobically/anaerobically in composting, but will continue to degrade in the soil or landfill. As long as water is present, they will continue to break down into low molecular weight fragments which can be ultimately biodegraded by microorganisms completely into biogas, biomass, and liquid leachate, as for natural organics like wood.

Polyesters have been considered for biodegradable articles and end uses in the past. Said biodegradable polyesters can be described as belonging to three general classes; aliphatic polyesters, aliphatic-aromatic polyesters and sulfonated aliphatic-aromatic polyesters.

Aliphatic polyesters are meant to include polyesters derived solely from aliphatic dicarboxylic acids, such as poly(ethylene succinate), poly(1,4-butylene adipate), and the like, as well as poly(hydroxyalkanates), such as polyhydroxybutyrate, polylactide, polycaprolactone, polyglycolide and the like. Representative art in the area of aliphatic polyesters includes, for example; Clendinning, et. al., in U.S. Pat. No. 3,932,319, Casey, et. al., in U.S. Pat. No. 4,076,798, Tokiwa, et. al., in U.S. Pat. No. 5,256,711, Buchanan, et. al., in U.S. Pat. Nos. 5,292,783, 5,559,171, 5,580,911, and 5,599,858, Tajima, et. al., in U.S. Pat. No. 5,300,572, Taka, et. al., in U.S. Pat. No. 5,324,794, Takahashi, in U.S. Pat. No. 5,349,028, Imaizumi, in U.S. Pat. No. 5,530,058, Itoh, et. al., in U.S. Pat. Nos. 5,391,700 and 5,616,681, Noda, et. al., in U.S. Pat. Nos. 5,653,930 and 5,780,368, Imaizumi, et. al., in U.S. Pat. No. 5,714,569, Kuroda, et. al., in U.S. Pat. No. 5,786,408, and Sugimoto, in U.S. Pat. No. 6,083,621.

Aliphatic-aromatic polyesters are meant to include polyesters derived from a mixture of aliphatic dicarboxylic acids and aromatic dicarboxylic acids. Representative teachings in the area of aliphatic-aromatic copolyesters include, for example; Sublett, et. al., in U.S. Pat. No. 3,948,859, Buxbaum, et. al., in U.S. Pat. No. 4,166,895, Horlbeck, et. al., in U.S. Pat. No. 4,328,059, Subleft, in U.S. Pat. No. 4,419,507, Buchanan, et. al., in U.S. Pat. No. 5,446,079, Gordon, et. al., in U.S. Pat. No. 5,594,076, Khemani, in U.S. Pat. Nos. 5,661,193 and 6,020,393, and Lorcks, et. al., in U.S. Pat. No. 6,096,809.

Sulfonated aliphatic-aromatic polyesters are meant to include polyesters derived from a mixture of aliphatic dicarboxylic acids and aromatic dicarboxylic acids and, in addition, incorporate a sulfonated monomer, such as the metal salts of 5-sulfoisophthalic acid. Representative art teachings in the area of sulfonated aliphatic-aromatic copolyesters includes, for example; King, et. al., in U.S. Pat. No. 3,936,389, Griffing, et. al., in U.S. Pat. No. 3,018,272, Kotera, et. al., in U.S. Pat. No. 4,340,519, Tung, in U.S. Pat. No. 4,390,687, Miller, in U.S. Pat. No. 4,394,442, Posey, et. al., in U.S. Pat. No. 4,476,189, U.S. Pat. Nos. 4,525,419, and 4,585,687, Tietz, in U.S. Pat. No. 5,053,482, Tietz, in U.S. Pat. No. 5,097,005, Gallagher, et. al., in U.S. Pat. No. 5,097,004, Gallagher, et. al., in U.S. Pat. No. 5,171,308, Romesser, et. al., in U.S. Pat. No. 5,295,985, Gallagher, et. al., in U.S. Pat. No. 5,171,309, Gallagher, et. al., in U.S. Pat. No. 5,219,646, Fish, et. al., in U.S. Pat. No. 5,354,616, Warzelhan, et. al., in U.S. Pat. Nos. 5,817,721, 5,880,220, 5,889,135, and 6,018,004, and Yamamoto, et. al., in U.S. Pat. No. 6,103,858.

Other Polyester Embodiments

Unsaturated polyesters are also known within the art. Reference is made to Jeffrey Selley in Encyclopedia of Chemical Technology, vol. 19. Fourth ed., Executive Editor, Jacqueline I. Kroschwitz, Editor, Mary Howe-Grant, pp. 654–678 (1996). Unsaturated polyesters which incorporate bis(2-hydroxyethyl)isosorbide of the present invention may be prepared as described therein.

Polyester polyols are known within the art. They are used, for example, in the preparation of coatings, paints and polyurethanes. Polyester polyols which incorporate bis(2-hydroxyethyl)isosorbide of the present invention may be produced by any known method in the art. Generally this includes adding a dicarboxylic acid component, a bis(2-hydroxyethyl)isosorbide component, an other glycol component and optionally a catalyst and a branching agent together, typically utilizing a molar excess of the glycol component, (the combination of the bis(2-hydroxyethyl) isosorbide component and the other glycol component), and heating to the desired molecular weight, typically as measured by the hydroxyl or acid number. The acid number is defined by DIN 53 402 and the hydroxyl number is defined by DIN 53 240. Typically, polyester polyols will preferably have molecular weights between 500 and 10,000, more preferably between 500 and 5,000. However, higher molecular weight polyester polyols are producible. Representative references include U.S. Pat. Nos. 3,994,851, 4,104,240, 4,243,705, 4,540,771, 4,888,441, 4,922,002, 5,976,706, 6,087,466, and 6,087,466, and the references cited therein. These references are hereby incorporated by reference in the present invention.

Polyester amides are known within the art. Polyester amides of the present invention which incorporate bis(2-hydroxyethyl)isosorbide are producible by any known methods in the art. Representative references include, for example, U.S. Pat. Nos. 4,709,004, 4,835,248, 5,349,011, 5,457,144, and the references cited therein.

Polyurethanes

A further aspect of the present invention includes polyurethanes which incorporate bis(2-hydroxyethyl)isosorbide. Said polyurethanes which incorporate bis(2-hydroxyethyl) isosorbide are comprised essentially of:

(a) 45.0 to 50.0 mole percent of a polyisocyanate component, (b) 50.0 to 0.1 mole percent of bis(2-hydroxyethyl) isosorbide, (c) 0 to 5.0 mole percent at least one polyester polyol, and (d) 0 to 49.9 mole percent of at least one additional glycol component.

Said polyisocyanate component is meant to include both polyisocyanates and chemically blocked isocyanates, such as with methanol, oximes such as methylethyl ketone oxime, lactams such as caprolactam, imidazole or phenols. Specific examples of useful polyisocyanate components includes diphenylmethane diisocyanate, toluene diisocyanate, xylene diisocyanate, phenylene diisocyanate, naphthalene diisocyanate, 4,4'-methylene-bis-(cyclohexyl isocyanate), isophorone diisocyanate, 1,6-hexamethylene diisocyanate, the biuret from 1,6-hexamethylene diisocyanate commercially available from Mobay Chemical Company as DESMODUR N, 1,12-dodecane diisocyanate and the like and mixtures thereof.

Said other glycol component is meant to include unsubstituted, substituted, straight chain, branched, cyclic aliphatic, aliphatic-aromatic or aromatic diols having from 2 carbon atoms to 36 carbon atoms and poly(alkylene ether) glycols with molecular weights between about 250 to 4,000. Specific examples of the desirable other glycol component include ethylene glycol, 1,3-propanediol, 1,2-propanediol, 1,2-butanediol, 1,3-butanediol, 1,3-2-methylpropanediol, neopentyl glycol, 1,4-butanediol, 1,3-hexanediol, 1,6-hexanediol, 2-ethyl-2-methyl-1,3-propanediol, 1,8-octanediol, 1,10-decanediol, 1,12-dodecanediol, 1,14-tetradecanediol, 1,16-hexadecanediol, dimer diol, 4,8-bis (hydroxymethyl)-tricyclo[5.2.1.0/2.6]decane, 1,4-cyclohexanedimethanol, di(ethylene glycol), tri(ethylene glycol), poly(ethylene ether) glycols, poly(butylene ether) glycols and the like and mixtures derived therefrom. This should not be taken as limiting. Essentially any other glycol known within the art may find use within the present invention.

Catalysts, for example, such as organotin compounds, may be employed in the polymerization reaction to form polyurethanes.

Methods to prepare polyurethanes are known within the art. Reference is made to a recent review by Henri Ulrich in Encyclopedia of Chemical Technology, vol. 24, fourth ed., Executive Editor, Jacqueline I. Kroschwitz, Editor, Mary Howe-Grant, pp. 695–726 (1996). Polyurethanes which incorporate bis(2-hydroxyethyl)isosorbide or polyester polyols which incorporate bis(2-hydroxyethyl)isosorbide of the present invention may be produced by any known method in the art. Representative art includes, for example U.S. Pat. Nos. 3,943,077, 4,139,501, 4,251,635, 4,258,141, 4,284,730, 4,317,889, 4,433,071, 6,087,466, 6,103,822, 6,111,048, 6,114,403, and the references cited therein.

Polyethers

Polyethers, including polyether sulfones and polyether ketones, are known within the art. The polyethers of the present invention, which includes polyether sulfones and polyether ketones which incorporate bis(2-hydroxyethyl) isosorbide, are producible by any known method in the art. Reference is made to Dwain M. White in Encyclopedia for Chemical Technology, vol. 19, fourth editions, Executive Editor, Jacqueline I. Kroschwitz, Editor, Mary Howe-Grant, pp. 678–701 (1996) and the references cited therein.

Polycarbonates

Polycarbonates and polycarbonate esters are known within the art. The polycarbonates and polycarbonate esters which incorporate bis(2-hydroxyethyl)isosorbide and polyester polyols which incorporate bis(2-hydroxyethyl) isosorbide of the present invention are producible by any known method of the art. Reference is made to Daniel J. Brunelle in Encyclopedia of Chemical Technology, volume 19, fourth edition, Executive Editor, Jacqueline I. Kroschwitz, Editor, Mary Howe-Grant, pp. 584–608 (1996) and the references cited therein. Further art references include, for example, U.S. Pat. Nos. 4,041,018, 4,104,217, 4,267,120, and the references cited therein.

Shaped Articles

As a further aspect of the present invention, the polymeric materials which incorporate bis(2-hydroxyethyl)isosorbide of the present invention have been found to be useful within a wide variety of shaped articles. Said polymeric materials of the present invention which incorporate bis(2-hydroxyethyl)isosorbide and/or polyester polyols which incorporate bis(2-hydroxyethyl)isosorbide may include, for example, polyesters, polyamide esters, polyurethanes, polycarbonates, polycarbonate esters, polyether sulfones, polyether ketones and the like. Examples of shaped articles include film, sheets, fiber, melt blown containers, molded parts, such as cutlery, foamed parts, polymeric melt extrusion coatings onto substrates, polymeric solution coatings onto substrates and the like. The polymeric materials which incorporate bis(2-hydroxyethyl)isosorbide of the present invention may be solution or melt processed to form coatings, films and the like. Coatings may be produced by coating a substrate with polymer solutions of the polymeric materials of the present invention followed by drying, by coextruding the polymeric materials of the present invention with other materials, or by melt coating a preformed substrate with the polymeric materials of the present invention. This should not be considered limiting. The polymeric materials of the present invention will find utility in essentially any process known within the art. Said coatings derived from the polymeric materials of the present invention will find utility as barriers to moisture, oxygen, carbon dioxide and the like. Said coatings derived from the polymeric materials of the present invention will also be useful as adhesives. Films of the polymeric materials of the present invention may be produced by any known art method, including, for example, solution or melt casting.

Films and Sheets

A further specific aspect of the present invention includes shaped articles in the form of films produced from polymeric materials which incorporate bis(2-hydroxyethyl)isosorbide. Said films and sheets of the present invention which incorporate bis(2-hydroxyethyl)isosorbide and/or polyester polyols which incorporate bis(2-hydroxyethyl)isosorbide may include, for example, polyesters, polyamide esters, polyurethanes, polycarbonates, polycarbonate esters, polyether sulfones, polyether ketones and the like.

Film Applications

Polymeric films have a variety of uses, such as in packaging, especially of foodstuffs, adhesives tapes, insulators, capacitors, photographic development, x-ray development and as laminates, for example. For many of these uses, the heat resistance of the film is an important factor. Therefore, a higher melting point and glass transition temperature are desirable to provide better heat resistance and more stable electrical characteristics. Further, it is desired that these films have good tensile strength and a high elongation at break.

The polymeric materials which incorporate bis(2-hydroxyethyl)isosorbide of the present invention may be formed into a film for use in any one of the many different applications, such as food packaging, labels, dielectric insulation, a water vapor barrier or the like. The monomer composition of the polymeric material is preferably chosen to result in a partially crystalline polymer desirable for the formation of film, wherein the crystallinity provides strength and elasticity. As first produced, the polymeric material is generally semi-crystalline in structure. The crystallinity increases on reheating and/or stretching of the polymer, as occurs in the production of film.

In the process of the invention, film is made from the polymer by any process known in the art. The difference between a film and a sheet is the thickness, but there is no set industry standard as to when a film becomes a sheet. For purposes of this invention, a film is less than or equal to 0.25 mm (10 mils) thick, preferably between about 0.025 mm and 0.15 mm (1 mil and 6 mils). However, thicker films can be formed up to a thickness of about 0.50 mm (20 mils).

Film Extrusion

The film of the present invention is preferably formed by either solution casting or extrusion. Extrusion is particularly preferred for formation of "endless" products, such as films and sheets, which emerge as a continuous length. In extrusion, the polymeric material, whether provided as a molten polymer or as plastic pellets or granules, is fluidized and homogenized. This mixture is then forced through a suitably shaped die to produce the desired cross-sectional film shape. The extruding force may be exerted by a piston or ram (ram extrusion), or by a rotating screw (screw extrusion), which operates within a cylinder in which the material is heated and plasticized and from which it is then extruded through the die in a continuous flow. Single screw, twin screw, and multi-screw extruders may be used as known in the art. Different kinds of die are used to produce different products, such as blown film (formed by a blow head for blown extrusions), sheets and strips (slot dies) and hollow and solid sections (circular dies). In this manner, films of different widths and thickness may be produced, and, in some cases, such as when film is used as a coating, it may be extruded directly onto the object to be coated. For example, wires and cables can be sheathed directly with polymeric films extruded from oblique heads. As a further example, laminated paper coatings can be produced by melt extruding the polymer directly onto paperboard. After extrusion, the polymeric film is taken up on rollers, cooled and taken off by means of suitable devices which are designed to prevent any subsequent deformation of the film.

Using extruders as known in the art, film can be produced by extruding a thin layer of polymer over chilled rolls and then further drawing down the film to size by tension rolls. Preferably, the finished film is less than or equal to 0.25 mm thick. Blown film, which is generally stronger, tougher, and made more rapidly than cast film, is made by extruding a tube. In producing blown film, the melt flow is turned upward from the extruder and fed through an annular die. As this tube leaves the die, internal pressure is introduced through the die mandrel with air, which expands the tube from about 1.5 to about 2.5 times the die diameter and simultaneously draws the film, causing a reduction in thickness. The resulting sleeve is subsequently slit along one side, making a larger film width than could be conveniently made via the cast film method. In extrusion coating, the substrate (paper, foil, fabric, polymeric film, and the like) is compressed together with the extruded polymeric melt by means of pressure rolls so that the polymer impregnates the substrate for maximum adhesion.

For manufacturing large quantities of film, a sheeting calender is employed. The rough film is fed into the gap of the calender, a machine comprising a number of heatable parallel cylindrical rollers which rotate in opposite directions and spread out the polymer and stretch it to the required thickness. The last roller smooths the film thus produced. If the film is required to have a textured surface, the final roller is provided with an appropriate embossing pattern. Alternatively, the film may be reheated and then passed through an embossing calender. The calender is followed by one or more cooling drums. Finally, the finished film is reeled up.

Alternatively, as mentioned previously, a supporting material may be coated directly with a film. For example, textile fabrics, paper, cardboard, metals, various building materials and the like, may be coated directly with the polymeric material for the purpose of electrical insulation, protection against corrosion, protection against the action of moisture or chemicals, impermeability to gases and liquids, or increasing the mechanical strength. One process to achieve this is referred to as melt extrusion of the polymeric melt onto a substrate. Coatings are applied to textiles, foil, and other sheet materials by continuously operating spread-coating machines. A coating knife, such as a "doctor knife", ensures uniform spreading of the coating materials (in the form of solution, emulsions, or dispersions in water or an organic medium) on the supporting material, which is moved along by rollers. The coating is then dried. Alternatively, when the coating is applied to the supporting material in the form of a polymeric film, the process is called laminating.

Metal articles can also be coated with the polymeric film by means of the whirl sintering process. The articles, heated to above the melting point of the polymer, are introduced into a fluidized bed of powdered polymer wherein the polymer particles are held in suspension by a rising stream of air, thus depositing a coating on the metal by sintering.

Extruded films may also be used as the starting material for other products. For example, the film may be cut into small segments for use as feed material for other processing methods, such as injection molding.

A film may also be made by solution casting, which produces more consistently uniform gauge film than that made by melt extrusion. Solution casting comprises dissolving polymeric granules, powder or the like in a suitable solvent with any desired formulant, such as a plasticizer or colorant. The solution is filtered to remove dirt or large particles and cast from a slot die onto a moving belt, preferably of stainless steel, dried, whereon the film cools. The extrudate thickness is five to ten times that of the finished film. The film may then be finished in a like manner to the extruded film.

One of ordinary skill in the art will be able to identify appropriate process parameters based on the polymeric composition and process used for film formation.

Sheet Applications

For purposes of this invention, a sheet is greater than about 0.25 mm (10 mils) thick, preferably between about 0.25 mm and 25 mm, more preferably from about 2 mm to about 15 mm, and even more preferably from about 3 mm to about 10 mm. In a preferred embodiment, the sheets of the present invention have a thickness sufficient to cause the sheet to be rigid, which generally occurs at about 0.50 mm and greater. However, sheets greater than 25 mm, and thinner than 0.25 mm may be formed.

Polymeric sheets have a variety of uses, such as in signage, glazing, (such as in bus stop shelters, sky lights or recreational vehicles), thermoforming articles, automobile lights, displays and display substrates, for example. For many of these uses, the heat resistance of the sheet is an important factor. Therefore, a higher melting point and glass transition temperature are desirable to provide better heat resistance and greater stability. Further, it is desired that these sheets have ultraviolet (UV) and scratch resistance, good tensile strength, high optical clarity, and good impact strength, particularly at low temperatures.

Various polymeric compositions have been used in an attempt to meet all of the above criteria. In particular, poly(ethylene terephthalate) (PET) has been used to form low-cost sheets for many years. However, these PET sheets have poor low temperature impact strength, a low glass transition temperature (Tg) and a high rate of crystallization. Thus, PET sheets cannot be used at low temperatures because of the danger of breakage and they cannot be used at high temperatures because the polymer crystallizes, thereby diminishing optical clarity.

Polycarbonate sheets can be used in applications where low temperature impact strength is needed, or a high service temperature is required. In this regard, polycarbonate sheets have high impact strengths at low temperatures as well as a high Tg which allows them to be used in high temperature applications. However, polycarbonate has poor solvent resistance, thereby limiting its use in certain applications, and is prone to stress induced cracking. Polycarbonate sheets also provide greater impact strength than is needed for certain applications, making them costly and inefficient for use.

Sheet Preparation

The polymeric sheets of the present invention may be formed by any process known in the art, such as extrusion, solution casting or injection molding. The parameters for each of these processes can be easily determined by one of ordinary skill in the art depending upon viscosity characteristics of the copolyester and the desired thickness of the sheet. The sheet of the present invention is preferably formed by either solution casting or extrusion as described above for film extrusion and film casting. Further, sheets and sheet-like articles, such as discs, may be formed by injection molding by any method known in the art.

The sheets of the present invention as described above may be thermoformed by any known method into any desirable shape, such as covers, skylights, shaped greenhouse glazing, displays, food trays, and the like. The thermoforming is accomplished by heating the sheet to a sufficient temperature and for sufficient time to soften the polymeric material of the present invention so that the sheet can be easily molded into the desired shape. In this regard, one of ordinary skill in the art can easily determine the optimal thermoforming parameters depending upon the viscosity and crystallization characteristics of the polymeric sheet.

Laminate and Multilayer Applications

The polymeric films and sheet of the invention may be combined with other polymeric materials during extrusion and/or finishing to form laminates or multilayer films and sheets with improved characteristics, such as water vapor resistance. In particular, the polymeric sheet of the invention may be combined with one or more of the following: poly(ethylene terephthalate) (PET), aramid, polyethylene sulfide (PES), polyphenylene sulfide (PPS), polyimide (PI), polyethylene imine (PEI), poly(ethylene naphthalate) (PEN), polysulfone (PS), polyether ether ketone (PEEK), olefins, polyethylene, poly(cyclic olefins), cellulose, polyamides, nylons, elastomers, poly(phenylene oxide) (PPO), and cyclohexylene dimethylene terephthalate and the like, for example. Other polymers may also find utility within the present invention. A multilayer or laminate sheet may be made by any method known in the art, and may have as many as five or more separate layers joined together by heat, adhesive and/or tie layer, as known in the art.

Post-forming Operations

The film and sheet extrusion processes of the invention can be combined with a variety of post-extruding operations for expanded versatility. Such post-forming operations include altering round to oval shapes, blowing the film or sheet to different dimensions, machining and punching, biaxial stretching and the like, as known to those skilled in the art.

Regardless of how the film or sheet is formed, it is desirably subjected to biaxial orientation by stretching in both the machine and transverse direction after formation. The machine direction stretch is initiated in forming the film or sheet simply by rolling out and taking up the film or sheet. This inherently stretches the film or sheet in the direction of take-up, orienting some of the fibers. Although this strengthens the film or sheet in the machine direction, it allows the film or sheet to tear easily in the direction at right angles because all of the fibers are oriented in one direction.

Therefore, biaxially stretched films and sheets are preferred for certain uses where uniformity is desired. Biaxial stretching orients the fibers parallel to the plane of the film or sheet, but leaves the fibers randomly oriented within the plane of the film or sheet. This provides superior tensile strength, flexibility, toughness and shrinkability, for example, in comparison to non-oriented films or sheets. It is desirable to stretch the film or sheet along two axes at right angles to each other. This increases tensile strength and elastic modulus in the directions of stretch. It is most desirable for the amount of stretch in each direction to be roughly equivalent, thereby providing similar properties or behavior within the film or sheet when tested from any direction.

The biaxial orientation may be obtained by any process known in the art. However, tentering is preferred, wherein the material is stretched while heating in the transverse direction simultaneously with, or subsequent to, stretching in the machine direction.

Shrinkage can be controlled by holding the sheet in a stretched position and heating for a few seconds before quenching. This heat stabilizes the oriented film or sheet, which then may be forced to shrink only at temperatures above the heat stabilization temperature.

Film and Sheet Properties

The properties exhibited by a film or sheet will depend on several factors indicated above, including the polymeric composition, the method of forming the polymer, the method of forming the film or sheet, and whether the film or sheet was treated for stretch or biaxially oriented. These factors affect many properties of the film or sheet, such as shrinkage, tensile strength, elongation at break, impact strength, dielectric strength and constant, tensile modulus, chemical resistance, melting point, heat deflection temperature, and the like.

The film or sheet properties may be further adjusted by adding certain additives and fillers to the polymeric composition, such as colorants, dyes, UV and thermal stabilizers, antioxidants, plasticizers, lubricants antiblock agents, slip agents, and the like, as recited above. Alternatively, the polymeric materials which incorporate bis(2-hydroxyethyl)isosorbide of the present invention may be blended with one or more other polymers, such as starch, elastomers, polyolefins, polyesters, polyamides, nylons, and the like to improve certain characteristics. Other polymers may be added to change such characteristics as air permeability, optical clarity, strength and/or elasticity, for example.

Containers

A further specific aspect of the present invention includes shaped articles in the form of containers produced from polymeric materials which incorporate bis(2-hydroxyethyl) isosorbide. Said polymeric materials of the present invention which incorporate bis(2-hydroxyethyl)isosorbide and/or polyester polyols which incorporate bis(2-hydroxyethyl) isosorbide may include, for example, polyesters, polyamide esters, polyurethanes, polycarbonates, polycarbonate esters, polyether sulfones, polyether ketones and the like.

Plastic containers are widely used for foods and beverages, and also for non-food materials. Poly(ethylene terephthalate) (PET) is used to make many of these containers because of its appearance (optical clarity), ease of blow molding, chemical and thermal stability, and its price. PET is generally fabricated into bottles by blow molding processes, and generally by stretch blow molding.

In stretch blow molding, PET is first shaped by injection molding into a thick-walled preformed parison (a "preform"), which typically is in the shape of a tube with a threaded opening at the top. The parison may be cooled and then used later in a subsequent step, or the process may be carried out in one machine with cooling just to the stretch blow molding temperature. In the stretch blow molding step, the parison is heated to a high enough temperature in a mold to allow shaping, but not so hot that it crystallizes or melts (i.e., just above the glass transition temperature Tg). The parison is expanded to fill the mold by rapidly stretching it mechanically in the axial direction (e.g.; by using a mandrel) while simultaneously forcing air under pressure into the heated parison to expand it radially. PET is typically modified for blow molding with a small amount of comonomer, usually 1,4-cyclohexanedimethanol or isophthalic acid, which increases the width of the temperature window for successful blow molding to about 9 C. The comonomer is necessary because of the need to have a wider temperature window, and also to decrease the rate of stress induced crystallization. At the same time, the comonomer may have the undesirable effect of lowering the glass transition temperature and reducing the crystallinity of PET. Stretch blow molding of PET, and blow molding processes in general, are well known in the art. Reviews are widely available, as for example, "Blow Molding" by C. Irwin in Encyclopedia of Polymer Science And Engineering, Second Edition, Vol. 2, John Wiley and Sons, New York, 1985, pp. 447–478.

The technology is widely used, but there are still improvements that need to be made. Containers which are derived from a renewable resource would be an improvement.

The containers described herein may be made by any method known in the art, such as extrusion, injection molding, injection blow molding, rotational molding, thermoforming of a sheet, and stretch-blow molding.

In the present invention, the preferred method for molding a container is stretch-blow molding, which generally used in the production of poly(ethylene terephthalate) (PET) containers, such as bottles. In this case, use may be made of any of the cold parison methods, in which a preformed parison (generally made by injection molding) is taken out of the mold and then subjected to stretch blow molding in a separate step. The hot parison method as known in the art may also be used, wherein the hot parison is immediately subjected to stretch blow molding in the same equipment without complete cooling after injection molding to make the parison. The parison temperature will vary based on the exact composition of the polymer to be used. Generally, parison temperatures in the range from about 90° C. to about 160° C. are found useful. The stretch blow molding temperature will also vary dependant on the exact material composition used, but a mold temperature of about 80° C. to about 150° C. is generally found to be useful.

Containers of the invention may have any shape desirable, and particularly include narrow-mouth bottles and wide-mouth bottles having threaded tops and a volume of about 400 mL to about 3 liters, although smaller and larger containers may be formed.

The containers can be used in standard cold fill applications. For some of the compositions of the present invention, hot fill applications may also be used.

The containers of the invention are suitable for foods and beverages, and other solids and liquids. The containers are normally clear and transparent, but can be modified to have color or to be opaque, rather than transparent, if desired, by adding colorants or dyes, or by causing crystallization of the polymer, which results in opaqueness.

Fibers

A further specific aspect of the present invention includes shaped articles in the form of fiber produced from polymeric materials which incorporate bis(2-hydroxyethyl)isosorbide. Said polymeric materials of the present invention which incorporate bis(2-hydroxyethyl)isosorbide and/or polyester polyols which incorporate bis(2-hydroxyethyl)isosorbide may include, for example, polyesters, polyamide esters, polyurethanes, polycarbonates, polycarbonate esters, polyether sulfones, polyether ketones and the like.

Polyester fibers are produced in large quantities for use inca variety of applications. In particular, these fibers are desirable for use in textiles, particularly in combination with natural fibers such as cotton and wool. Clothing, rugs, and other items may be fashioned from these fibers. Further, polyester fibers are desirable for use in industrial applications due to their elasticity and strength. In particular, they are used to make articles such as tire cords and ropes.

The term "fibers" as used herein is meant to include continuous monofilaments, non-twisted or entangled multifilament yarns, staple yarns, spun yarns, and non-woven materials. Such fibers may be used to form uneven fabrics, knitted fabrics, fabric webs, or any other fiber-containing structures, such as tire cords.

Synthetic fibers, such as nylon, acrylic, polyesters, polyurethanes, and others, are made by spinning and drawing the polymer into a filament, which is then formed into a yarn by winding many filaments together. These fibers are often treated mechanically and/or chemically to impart desirable characteristics such as strength, elasticity, heat resistance, hand (feel of fabric), and the like as known in the art based on the desired end product to be fashioned from fibers.

The monomer composition of the polymeric materials which incorporates bis(2-hydroxyethyl)isosorbide of the present invention is desirably chosen to result in a partially crystalline polymer. The crystallinity is desirable for the formation of fibers, providing strength and elasticity. As first produced, the polymeric material is mostly amorphous in structure. In preferred embodiments, the polymer readily crystallizes on reheating and/or extension of the polymer.

In the process of the invention, fibers are made from the polymer by any process known in the art. Generally, however, melt spinning is preferred for polymer fibers.

Melt spinning, which is most commonly used for polyesters, such as poly(ethylene terephthalate), polyurethanes, and nylons comprises heating the polymer to form a molten liquid, or melting the polymer against a heated surface. The molten polymer is forced through a spinneret with a plurality of fine holes. Upon contact with air or a non-reactive gas stream after passing through the spinneret, the polymer solution from each spinneret solidifies into filaments. The filaments are gathered together downstream from the spinneret by a convergence guide, and may be taken up by a roller or a plurality of rollers. This process allows filaments of various sizes and cross sections to be formed, including filaments having a round, elliptical, square, rectangular, lobed or dog-boned cross section, for example.

Following the extrusion and uptake of the fiber, the fiber is usually drawn, thereby increasing the crystallization and maximizing desirable properties such as orientation along the longitudinal axis, which increases elasticity, and strength. The drawing may be done in combination with take-up by using a series of rollers, some of which are generally heated, as known in the art, or may be done as a separate stage in the process of fiber formation.

The polymer may be spun at speeds of from about 600 to 6000 meters per minute or higher, depending on the desired fiber size. For textile applications, a fiber with a denier per filament of from about 0.1 to about 100 is desired. Preferably, the denier is about 0.5 to 20, more preferably 0.7 to 10. However, for industrial applications the fiber should be from about 0.5 to 100 denier per filament, preferably about 1.0 to 10.0, most preferably 3.0 to 5.0 denier per filament. The required size and strength of a fiber can be readily be determined by one of ordinary skill in the art for any given application.

The resulting filamentary material is amenable to further processing through the use of additional processing equipment, or it may be used directly in applications requiring a continuous filament textile yarn. If desired, the filamentary material subsequently may be converted from a flat yarn to a textured yarn through known false twist texturing conditions or other processes known in the art. In particular, it is desirable to increase the surface area of the fiber to provide a softer feel and to enhance the ability of the fibers to breathe, thereby providing better insulation and water retention in the case of textiles, for example. The fibers may therefore be crimped or twisted by the false twist method, air jet, edge crimp, gear crimp, or stuffer box, for example. Alternatively, the fibers may be cut into shorter lengths, called staple, which may be processed into yarn. A skilled artisan can determine the best method of crimping or twisting based on the desired application and the composition of the fiber.

After formation, the fibers are finished by any method appropriate to the desired final use. In the case of textiles, this may include dyeing, sizing, or addition of chemical agents such as antistatic agents, flame retardants, UV light stabilizers, antioxidants, pigments, dyes, stain resistants, antimicrobial agents and the like, which are appropriate to adjust the look and hand of the fibers. For industrial applications, the fibers may be treated to impart additional desired characteristics such as strength, elasticity or shrinkage, for example.

The continuous filament fiber of the invention may be used either as produced or texturized for use in a variety of applications such as textile fabrics for apparel and home furnishings, for example. High tenacity fiber can be used in industrial applications such as high strength fabrics, tarpaulins, sail cloth, sewing threads and rubber reinforcement for tires and V-belts, for example.

The staple fiber of the invention may be used to form a blend with natural fibers, especially cotton and wool. In particular, the polymeric materials form a chemically resistant fiber which is generally resistant to mold, mildew, and other problems inherent to natural fibers. The polymer fiber further provides strength and abrasion resistance and lowers the cost of material. Therefore, it is ideal for use in textiles and other commercial applications, such as for use in fabrics for apparel, home furnishings and carpets.

Further, the polymer of the invention may be used with another synthetic or natural polymer to form heterogeneous fiber, thereby providing a fiber with improved properties. The heterogeneous fiber may be formed in any suitable manner, such as side-by-side, sheath-core, and matrix designs, as is known within the art.

Processes to produce polyurethane fibers are known within the art. See, for example, U.S. Pat. No. 6,096,252 and the references cited therein.

Shaped Foamed Articles

A further specific aspect of the present invention includes shaped foamed articles produced from the polymeric materials which incorporate bis(2-hydroxyethyl)isosorbide. Said polymeric materials of the present invention which incorporate bis(2-hydroxyethyl)isosorbide and/or polyester polyols which incorporate bis(2-hydroxyethyl)isosorbide may include, for example, polyesters, polyamide esters, polyurethanes, polycarbonates, polycarbonate esters, polyether sulfones, polyether ketones and the like.

Thermoplastic polymeric materials are foamed to provide low density articles, such as films, cups, food trays, decorative ribbons, furniture parts and the like. For example, polystyrene beads containing low boiling hydrocarbons, such as pentane, are formed into light weight foamed cups for hot drinks such as coffee, tea, hot chocolate and the like. Polypropylene can be extruded in the presence of blowing agents such as nitrogen or carbon dioxide gas to provide decorative films and ribbons for package wrappings. Also, polypropylene can be injection molded in the presence of blowing agents to form lightweight furniture parts such as table legs and to form lightweight chairs.

Polyesters, such as poly(ethylene terephthalate), typically have a much higher density, (e.g.; 1.3 g/cc), than other polymers. It would, therefore, be desirable to be able to foam polyester materials to decrease the weight of molded parts, films, sheets, food trays, thermoformed parts and the like. Such foamed articles also provide improved insulating properties than unfoamed articles.

It has been generally been found in the art that the polyester to be foamed should desirably have a high melt viscosity. This is desired in order to have sufficient melt viscosity to hold the as formed foamed shape sufficiently long for the polyester to solidify to form the final foamed article. This can be achieved by raising the as produced polyester inherent viscosity through post-polymerization processes, such as the solid state polymerization method, as described above. Alternatively, the polyester may incorporate a branching agent, such as described in U.S. Pat. Nos. 4,132,707, 4,145,466, 4,999,388, 5,000,991, 5,110,844, 5,128,383, and 5,134,028. Such branched polyesters may additionally be subjected to the solid state polymerization, as described above, to further enhance the melt viscosity. It has also been found that the incorporation of sulfonate substituents onto the polyester backbone raise the apparent melt viscosity of the polyester, providing an adequately foamable polyester. More recently, it has been suggested that such sulfonated polyesters may be reacted with divalent cations to enhance the melt viscosity even greater, allowing for more desirable foamable polyesters, (see, for example, U.S. Pat. No. 5,922,782).

The polyesters of the present invention may be readily foamed by a wide variety of methods. These include the injection of an inert gas such as nitrogen or carbon dioxide into the melt during extrusion or molding operations. Alternatively, inert hydrocarbon gases such as methane, ethane, propane, butane, and pentane, or chlorofluorocarbons, hydrochlorofluorocarbons, hydrofluorocarbons, and the like may be used. Another method involves the dry blending of chemical blowing agents with the polyester and then extruding or molding the compositions to provide foamed articles. During the extrusion or molding operation, an inert gas such as nitrogen is released from the blowing agents and provides the foaming action. Typical blowing agents include azodicarbonamide, hydrazocarbonamide, dinitrosopentamethylenetetramine, p-toluenesulfonyl hydrazodicarboxylate, 5-phenyl-3,6-dihydro-1,3,4-oxa-diazin-2-one, sodium borohydride, sodium bicarbonate, 5-phenyltetrazole, p,p'-oxybis (benzenesulfonylhydrazide) and the like. Still another method involves the blending of sodium carbonate or sodium bicarbonate with one portion of the polyester pellets, blending of an organic acid, such as citric acid, with another portion of the polyester pellets and then blending of the two types of pellets through extrusion or molding at elevated temperatures. Carbon dioxide gas is released from the interaction of the sodium carbonate and citric acid to provide the desired foaming action in the polymeric melt.

It is desirable that the foamable polyester compositions incorporate nucleation agents to create sites for bubble initiation, influence the cell size of the foamed sheet or object and to hasten the solidification of the as foamed article. Examples of said nucleation agents may include sodium acetate, talc, titanium dioxide, polyolefin materials such as polyethylene, polypropylene, and the like.

Polymeric foaming equipment and processes are generally known within the art. See, for example, U.S. Pat. Nos. 5,116,881, 5,134,028, 4,626,183, 5,128,383, 4,746,478, 5,110,844, 5,000,844, and 4,761,256. Additional reviews on foaming technology may be found in Kirk-Othmer Encyclopedia of Chemical Technology, Third Edition, Volume 11, pp. 82–145 (1980), John Wiley and Sons, Inc., New York, N.Y. and the Encyclopedia of Polymer Science and Engineering, Second Edition, Volume 2, pp. 434–446 (1985), John Wiley and Sons, Inc., New York, N.Y. These references are herein incorporated into the present invention.

As described above, the foamable polyester compositions may include a wide variety of additives, fillers, or be blended with other materials. For biodegradable foams, the addition of starch, starch derivatives, cellulose and cellulose derivatives is especially preferred.

Polyurethane foams are known within the art. Representative references include, for example, U.S. Pat. No. 4,139,501, 4,284,730, 4,317,889, 4,365,025, 4,374,207, 4,384,051, 4,451,588, 4,529,742, 4,535,096, 4,668,708, 5,023,280, 5,059,633, 5,063,253, 5,100,925, 5,270,348, 5,369,138, 5,397,811, 5,418,261, 5,506,278, 5,536,757, 6,107,355, 6,114,402 6,114,403, 6,117,917, and the references cited therein. Polyurethane foams of the present invention which incorporate bis(2-hydroxyethyl)isosorbide and/or polyester polyols which incorporate bis(2-hydroxyethyl)isosorbide may be produced by any known method in the art.

EXAMPLES

Test Methods

Differential Scanning Calorimetry, (DSC), is performed on a TA Instruments Model Number 2920 machine. Samples are heated under a nitrogen atmosphere at a rate of 20 degrees C./minute to 300 degrees C., programmed cooled back to room temperature at a rate of 20 degrees C./minute and then reheated to 300 degrees C. at a rate of 20 degrees C./minute. The observed sample glass transition temperature, (Tg), and crystalline melting temperature, (Tm), noted below were from the second heat.

Inherent Viscosity, (IV), is defined in "Preparative Methods of Polymer Chemistry", W. R. Sorenson and T. W. Campbell, 1961, p. 35. It is determined at a concentration of 0.5 g/100 mL of a 50:50 weight percent trifluoroacetic acid:dichloromethane acid solvent system at room temperature by a Goodyear R-103B method.

Biodegradation is performed according to the ISO 14855 method: "Determination of the ultimate aerobic biodegradability and disintegration of plastic materials under controlled composting conditions—Method by analysis of evolved carbon". This test involved injecting an inoculum consisting of a stabilized and mature compost derived from the organic fraction of municipal solid waste with ground powder of the polymer to be tested, composting under standard conditions at an incubation temperature controlled at 58° C. +/−2° C. The test is conducted with one polymer sample. The carbon dioxide evolved is used to determine the extent of biodegradation.

Example 1

To a reactor is charged isosorbide, (146.14 grams), ethylene carbonate, (184.93 grams), and potassium carbonate, (1.66 grams). The reactor is purge with nitrogen and then is slowly heated with stirring to 150° C. with a slight nitrogen purge. The resulting reaction mixture is stirred at 150° C. with a slight nitrogen purge until the carbon dioxide evolution ceases. The resulting reaction mixture is then stirred an additional hour at 150° C. with a slight nitrogen purge. The resulting reaction product is allowed to cool to room temperature.

The as produced reaction product is purified through vacuum distillation to provide the bis(2-hydroxyethyl) isosorbide product.

Example 2

To a 200 gallon autoclave is charged dimethyl terephthalate, (126.16 pounds), bis(2-hydroxyethyl) isosorbide, (152.11 pounds), manganese(II) acetate tetrahydrate, (37.65 grams), and antimony(III) trioxide, (13.6 grams). The autoclave is purged three times with nitrogen and heated to 245° C. over 4.5 hours with stirring. Over this heating cycle, distillate is recovered. With continued heating and stirring, vacuum is staged onto the autoclave over 1.5 hours. The resulting reaction mixture is stirred at 275° C. under full vacuum, (pressure equal to or less than 2 mm Hg) for 4 hours. The vacuum is then released and the resulting reaction mixture is extruded out of the autoclave as a ribbon, the polymer ribbon is cooled and chopped.

The polymer is tested for inherent viscosity, as described above and is found to have an IV greater than 0.35 dL/g.

Comparative Example CE1

To a 200 gallon autoclave is charged dimethyl terephthalate, (126.16 pounds), isosorbide, (9.5 pounds), ethylene glycol, (73.4 pounds), manganese(II) acetate tetrahydrate, (37.65 grams), and antimony(III) trioxide, (13.6 grams). The autoclave is purged three times with nitrogen and heated to 245° C. over 4.5 hours with stirring. Over this heating cycle, distillate is recovered. With continued heating and stirring, vacuum is staged onto the autoclave over 1.5 hours. The resulting reaction mixture is stirred at 275° C. under full vacuum (pressure equal to or less than 2 mm Hg) for 4 hours. The vacuum is then released and the resulting reaction mixture is extruded out of the autoclave as a ribbon, the polymer ribbon is cooled and chopped.

The polymer is tested for inherent viscosity, as described above and is found to have an IV greater than 0.35 dL/g.

The polymer is analyzed for composition with proton NMR and found to essentially incorporate 2.5 mole percent isosorbide. This would suggest that 50 percent of the added isosorbide is incorporated within the polymer.

Example 3

To a 200 gallon autoclave is charged dimethyl terephthalate, (126.16 pounds), bis(2-hydroxyethyl) isosorbide, (15.22 pounds), ethylene glycol, (73.4 pounds), manganese(II) acetate tetrahydrate, (37.65 grams), and antimony(III) trioxide, (13.6 grams). The autoclave is purged three times with nitrogen and heated to 245° C. over 4.5 hours with stirring. Over this heating cycle, distillate is recovered. With continued heating and stirring, vacuum is staged onto the autoclave over 1.5 hours. The resulting reaction mixture is stirred at 275° C. under full vacuum (pressure equal to or less than 2 mm Hg) for 4 hours. The vacuum is then released and the resulting reaction mixture is extruded out of the autoclave as a ribbon, the polymer ribbon is cooled and chopped.

The polymer is tested for inherent viscosity, as described above and is found to have an IV greater than 0.35 dL/g.

The polymer is analyzed for composition with proton NMR and found to essentially incorporate 5 mole percent bis(2-hydroxyethyl)isosorbide. This would suggest that essentially 100 percent of the added bis(2-hydroxyethyl) isosorbide is incorporated within the polymer.

The above prepared polymer of the present invention is found to have essentially quantitative incorporation of the bis(2-hydroxyethyl)isosorbide monomer. This is twice the incorporation rate of the isosorbide monomer into comparable polymers such as Comparative Example CE1.

Example 4

To a 200 gallon autoclave is charged dimethyl terephthalate, (98.4 pounds), dimethyl 5-sulfoisophthalate, sodium salt, (3.8 pounds), dimethyl glutarate, (20.8 pounds), bis(2-hydroxyethyl)isosorbide, (15.22 pounds), ethylene glycol, (73.4 pounds), manganese(II) acetate tetrahydrate, (37.65 grams), and antimony(III) trioxide, (13.6 grams). The autoclave is purged three times with nitrogen and heated to 245° C. over 4.5 hours with stirring. Over this heating cycle, distillate is recovered. With continued heating and stirring, vacuum is staged onto the autoclave over 1.5 hours. The resulting reaction mixture is stirred at 275° C. under full vacuum (pressure equal to or less than 2 mm Hg) for 4 hours. The vacuum is then released and the resulting reaction mixture is extruded out of the autoclave as a ribbon, the polymer ribbon is cooled and chopped.

The polymer is tested for inherent viscosity, as described above and is found to have an IV greater than 0.35 dL/g.

The polymer is analyzed for composition with proton NMR and found to essentially incorporate 5 mole percent bis(2-hydroxyethyl)isosorbide. This would suggest that essentially 100 percent of the added bis(2-hydroxyethyl)isosorbide is incorporated within the polymer.

The above prepared polymer is ground to powder and subjected to a biodegradation test as detailed above. This copolyester of the present invention is found to biodegrade.

Example 5

To a 200 gallon autoclave is charged dimethyl isophthalate, (126.11 pounds), bis(2-hydroxyethyl)isosorbide, (152.11 pounds), manganese(II) acetate tetrahydrate, (37.65 grams), and antimony(III) trioxide, (13.6 grams). The autoclave is purged three times with nitrogen and heated to 245° C. over 4.5 hours with stirring. Over this heating cycle, distillate is recovered. With continued heating and stirring, vacuum is staged onto the autoclave over 1.5 hours. The resulting reaction mixture is stirred at 275° C. under full vacuum (pressure equal to or less than 2 mm Hg) for 4 hours. The vacuum is then released and the resulting reaction mixture is extruded out of the autoclave as a ribbon, the polymer ribbon is cooled and chopped.

The polymer is tested for inherent viscosity, as described above and is found to have an IV greater than 0.35 dL/g.

Example 6

To a 200 gallon autoclave is charged dimethyl adipate, (113.2 pounds), bis(2-hydroxyethyl)isosorbide, (15.22 pounds), ethylene glycol, (73.4 pounds), manganese(II) acetate tetrahydrate, (37.65 grams), and antimony(III) trioxide, (13.6 grams). The autoclave is purged three times with nitrogen and heated to 245° C. over 4.5 hours with stirring. Over this heating cycle, distillate is recovered. With continued heating and stirring, vacuum is staged onto the autoclave over 1.5 hours. The resulting reaction mixture is stirred at 275° C. under full vacuum (pressure equal to or less than 2 mm Hg) for 4 hours. The vacuum is then released and the resulting reaction mixture is extruded out of the autoclave as a ribbon, the polymer ribbon is cooled and chopped.

The polymer is tested for inherent viscosity, as described above and is found to have an IV greater than 0.35 dL/g.

The polymer is analyzed for composition with proton NMR and found to essentially incorporate 5 mole percent bis(2-hydroxyethyl)isosorbide. This would suggest that essentially 100 percent of the added bis(2-hydroxyethyl)isosorbide is incorporated within the polymer.

Example 7

To a 200 gallon autoclave is charged dimethyl 2,6-naphthalenedicarboxylate, (158.68 pounds), bis(2-hydroxyethyl)isosorbide, (152.11 pounds), manganese(II) acetate tetrahydrate, (37.65 grams), and antimony(III) trioxide, (13.6 grams). The autoclave is purged three times with nitrogen and heated to 245° C. over 4.5 hours with stirring. Over this heating cycle, distillate is recovered. With continued heating and stirring, vacuum is staged onto the autoclave over 1.5 hours. The resulting reaction mixture is stirred at 275° C. under full vacuum (pressure equal to or less than 2 mm Hg) for 4 hours. The vacuum is then released and the resulting reaction mixture is extruded out of the autoclave as a ribbon, the polymer ribbon is cooled and chopped.

The polymer is tested for inherent viscosity, as described above and is found to have an IV greater than 0.35 dL/g.

Example 8

To a 200 gallon autoclave is charged dimethyl terephthalate, (98.1 pounds), dimethyl 5-sulfoisophthalate, sodium salt, (3.8 pounds), dimethyl succinate, (19.0 pounds), trimethyl 1,2,4-benzenetricarboxylate, (0.4 pounds), bis(2-hydroxyethyl)isosorbide, (15.2 pounds), ethylene glycol, (73.4 pounds), manganese(II) acetate tetrahydrate, (37.65 grams), and antimony(III) trioxide, (13.6 grams). The autoclave is purged three times with nitrogen and heated to 245° C. over 4.5 hours with stirring. Over this heating cycle, distillate is recovered. With continued heating and stirring, vacuum is staged onto the autoclave over 1.5 hours. The resulting reaction mixture is stirred at 275° C. under full vacuum, (pressure equal to or less than 2 mm Hg), for 4 hours. The vacuum is then released and the resulting reaction mixture is extruded out of the autoclave as a ribbon, the polymer ribbon is cooled and chopped.

The polymer is tested for inherent viscosity, as described above and is found to have an IV greater than 0.35 dL/g.

The polymer is analyzed for composition with proton NMR and found to essentially incorporate 5 mole percent bis(2-hydroxyethyl)isosorbide. This would suggest that essentially 100 percent of the added bis(2-hydroxyethyl)isosorbide is incorporated within the polymer.

Example 9

To a 200 gallon autoclave is charged dimethyl terephthalate, (60.6 pounds), dimethyl adipate, (56.6 pounds), bis(2-hydroxyethyl)isosorbide, (29.83 pounds), ethylene glycol, (61.3 pounds), manganese(II) acetate tetrahydrate, (37.65 grams), and antimony(III) trioxide, (13.6 grams). The autoclave is purged three times with nitrogen and heated to 245° C. over 4.5 hours with stirring. Over this heating cycle, distillate is recovered. With continued heating and stirring, vacuum is staged onto the autoclave over 1.5 hours. The resulting reaction mixture is stirred at 275° C. under full vacuum (pressure equal to or less than 2 mm Hg) for 4 hours. The vacuum is then released and the resulting reaction mixture is extruded out of the autoclave as a ribbon, the polymer ribbon is cooled and chopped.

The polymer is tested for inherent viscosity, as described above and is found to have an IV greater than 0.35 dL/g.

The polymer is analyzed for composition with proton NMR and found to essentially incorporate 10 mole percent bis(2-hydroxyethyl)isosorbide. This would suggest that essentially 100 percent of the added bis(2-hydroxyethyl)isosorbide is incorporated within the polymer.

The above prepared polymer is ground to powder and subjected to a biodegradation test as detailed above. This copolyester of the present invention is found biodegrade.

Example 10

To a 200 gallon autoclave is charged dimethyl terephthalate, (73.8 pounds), dimethyl adipate, (22.6 pounds), isophthalic acid, (21.0 pounds), bis(2-hydroxyethyl)isosorbide; (29.78 pounds), ethylene glycol, (61.3 pounds), manganese(II) acetate tetrahydrate, (37.65 grams), and antimony(III) trioxide, (13.6 grams). The autoclave is purged three times with nitrogen and heated to 245° C. over 4.5 hours with stirring. Over this heating cycle, distillate is recovered. With continued heating and stirring, vacuum is staged onto the autoclave over 1.5 hours. The resulting reaction mixture is stirred at 275° C. under full vacuum (pressure equal to or less than 2 mm Hg) for 4 hours. The vacuum is then released and the resulting reaction mixture is extruded out of the autoclave as a ribbon, the polymer ribbon is cooled and chopped.

The polymer is tested for inherent viscosity, as described above and is found to have an IV greater than 0.35 dL/g.

The polymer is analyzed for composition with proton NMR and found to essentially incorporate 10 mole percent isosorbide. This would suggest that essentially 100 percent of the added bis(2-hydroxyethyl)isosorbide is incorporated within the polymer.

The above prepared polymer is ground to powder and subjected to a biodegradation test as detailed above. This copolyester of the present invention was found to biodegrade.

1.1 grams of this polymer of the present invention is dissolved in 10.0 grams of tetrahydrofuran at room temperature. After mixing for 4 hours at room temperature, a clear solution is obtained. The solution is poured into a 2-inch diameter aluminum pan and allowed to dry at room temperature overnight. The resulting film is clear and pliable.

Example 11

To a 5 gallon autoclave is charged terephthalic acid, (14.9 pounds), adipic acid, (3.4 pounds), bis(2-hydroxyethyl) isosorbide, (2.7 pounds), ethylene glycol, (13.5 pounds), cobalt(II) acetate tetrahydrate, (1.83 grams), and antimony (III) trioxide, (3.10 grams). The polymerization autoclave is equipped with a fractional distillation column and a stirrer. The autoclave is purged three times with nitrogen, closed under 50 psig of nitrogen pressure and heated to 265° C. over 5 hours with stirring. The pressure rises to 70 psig during this time, as esterification takes place. At the end of this time period, the pressure is vented back to psig. Water and ethylene glycol distill from the autoclave. The temperature is maintained at 265° C. Within an hour, the contents of the autoclave are a clear, viscous melt. The excess pressure in the autoclave is then vented. A solution of ethylene glycol and polyphosphoric acid (3.45 weight percent phosphorous) is pumped into the autoclave. With continued heating and stirring, vacuum is staged onto the autoclave. The autoclave is then heated to 275° C. The resulting reaction mixture is stirred at 275° C. under full vacuum (pressure equal to or less than 2 mm Hg), for 4 hours. The vacuum is then released and the resulting reaction mixture is extruded out of the autoclave as a ribbon, the polymer ribbon is cooled and chopped.

The polymer is tested for inherent viscosity, as described above and is found to have an IV greater than 0.35 dL/g.

This polymer is tested for glass transition temperature by the above mentioned DSC test.

Example 12

To a 200 gallon autoclave is charged dimethyl 2,6-naphthalenedicarboxylate, (92.1 pounds), dimethyl adipate, (45.3 pounds), bis(2-hydroxyethyl)isosorbide, (30.4 pounds), ethylene glycol, (61.3 pounds), manganese(II) acetate tetrahydrate, (37.65 grams), and antimony(III) trioxide, (13.6 grams). The autoclave is purged three times with nitrogen and heated to 245° C. over 4.5 hours with stirring. Over this heating cycle, distillate is recovered. With continued heating and stirring, vacuum is staged onto the autoclave over 1.5 hours. The resulting reaction mixture is stirred at 275° C. under full vacuum (pressure equal to or less than 2 mm Hg) for 4 hours. The vacuum is then released and the resulting reaction mixture is extruded out of the autoclave as a ribbon, the polymer ribbon is cooled and chopped.

The polymer is tested for inherent viscosity, as described above and is found to have an IV greater than 0.35 dL/g.

Example 13

To a 200 gallon autoclave is charged dimethyl terephthalate, (60.6 pounds), dimethyl adipate, (56.6 pounds), bis(2-hydroxyethyl)isosorbide, (30.4 pounds), 1,4-butanediol, (75.0 pounds), and titanium(IV) isopropoxide, (19.57 grams). The autoclave is purged three times with nitrogen and heated to 245° C. over 4.5 hours with stirring. Over this heating cycle, distillate is recovered. With continued heating and stirring, vacuum is staged onto the autoclave over 1.5 hours. The resulting reaction mixture is stirred at 255° C. under full vacuum (pressure equal to or less than 2 mm Hg) for 4 hours. The vacuum is then released and the resulting reaction mixture is extruded out of the autoclave as a ribbon, the polymer ribbon is cooled and chopped.

The polymer is tested for inherent viscosity, as described above and is found to have an IV greater than 0.35 dL/g.

The above prepared polymer is ground to powder and subjected to a biodegradation test as detailed above. This copolyester of the present invention was found to biodegrade.

Example 14

To a 200 gallon autoclave is charged dimethyl terephthalate, (60.6 pounds), dimethyl adipate, (56.6 pounds), bis(2-hydroxyethyl)isosorbide, (30.4 pounds), 1,3-propanediol, (63.3 pounds), and titanium(IV) isopropoxide, (19.57 grams). The autoclave is purged three times with nitrogen and heated to 245° C. over 4.5 hours with stirring. Over this heating cycle, distillate is recovered. With continued heating and stirring, vacuum is staged onto the autoclave over 1.5 hours. The resulting reaction mixture is stirred at 255° C. under full vacuum (pressure equal to or less than 2 mm Hg) for 4 hours. The vacuum is then released and the resulting reaction mixture is extruded out of the autoclave as a ribbon, the polymer ribbon is cooled and chopped.

The polymer is tested for inherent viscosity, as described above and is found to have an IV greater than 0.35 dL/g.

Example 15

To a 200 gallon autoclave is charged dimethyl terephthalate, (126.16 pounds), bis(2-hydroxyethyl) isosorbide, (7.61 pounds), ethylene glycol, (73.4 pounds), manganese(II) acetate tetrahydrate, (37.65 grams), and antimony(III) trioxide, (13.6 grams). The autoclave is purged three times with nitrogen and heated to 245° C. over 4.5 hours with stirring. Over this heating cycle, distillate is recovered. With continued heating and stirring, vacuum is staged onto the autoclave over 1.5 hours. The resulting reaction mixture is stirred at 275° C. under full vacuum (pressure equal to or less than 2 mm Hg) for 4 hours. The vacuum is then released and the resulting reaction mixture is extruded out of the autoclave as a ribbon, the polymer ribbon is cooled and chopped.

The polymer is tested for inherent viscosity, as described above and is found to have an IV greater than 0.35 dL/g. Its Tg is found by DSC to be above the Tg of a comparative polyester without the isosorbide derivative.

The polymer is analyzed for composition with proton NMR and found to essentially incorporate 2.5 mole percent bis(2-hydroxyethyl)isosorbide. This would suggest that essentially 100 percent of the added bis(2-hydroxyethyl) isosorbide is incorporated within the polymer.

Example 16

To a 2 liter three necked glass flask was added adipic acid, (438.42 grams), bis(2-hydroxyethyl)isosorbide, (234.14 grams), di(ethylene glycol), (106.12 grams), and 1,4-butanediol, (225.30 grams). With stirring, the reaction mixture was slowly heated to a final temperature of 200° C. under a slight nitrogen purge. Vacuum (pressure=10–15 mmHg) was applied while the reaction was stirring and heating were allowed to continue. Distillates were collected until a molecular weight of 2000 was achieved, as is measurable by the acid value (KOH mg/g). The resulting polyester polyol was allowed to cool to room temperature.

Example 17

A reactor is charged with bis(2-hydroxyethyl)isosorbide, (234.14 grams). The reaction mixture is heated to 70° C. with stirring under a slight nitrogen purge. Tolylene 2,6-diisocyanate, (174.16 grams), is dropwise added over 1 hour to the stirred reaction mixture at 70° C. The resulting reaction mixture is allowed to stir for an additional hour at 70° C. and then the resulting polyurethane product is allowed to cool to room temperature and recovered.

Example 18

A reactor is charged with the polyester polyol prepared in Example 16, (200.00 grams). The reaction mixture is heated to 70° C. with stirring under a slight nitrogen purge. 4,4'-Methylenebis(phenyl isocyanate), (25.03 grams), is dropwise added over 1 hour to the stirred reaction mixture at 70° C. The resulting reaction mixture is allowed to stir for an additional hour at 70° C. and then the resulting polyurethane product is allowed to cool to room temperature and recovered.

Example 19

The polymer of the present invention produced in Example 15, above, is extruded as a film using a Killion PL 100 Film extrusion line. The processing conditions are as follows:

| Extruder Barrel Temperature | |
| --- | --- |
| zone 1 | 190° C. |
| zone 2 | 270° C. |
| zone 3 | 280° C. |
| zone 4 | 280° C. |
| Clamp ring temperature | 280° C. |
| Adaptor temperature (inlet) | 290° C. |
| Melt pump temperature | 290° C. |
| Melt pump rpm | 10 |
| Throughput | 3 lb./hr. |
| Adapter temperature (outlet) | 280° C. |
| Extruder melt pressure | ~1500 psi |
| Die adapter temperature | 290° C. |
| Die temperature | 290° C. |
| Die Lip temperature | 290° C. |
| Die gap | 0.25 mm (10 mil) |
| Die size | 4-inch |
| Casting temperature | 50° C. |
| Casting speed | 5 & 3 m/min. |
| Filter size | 25 microns |

The film exiting the die is 4 inches wide and 0.10 mm (4 mils) thick.

The extruded film is stretched uniaxially and biaxially using a modified Bruckner Stretching Frame (Bruckner, Siegsdorf, Germany). The sample is inserted with the machine direction (MD) on the Y axis of the machine. Draw speed is 1.50 in/sec. Typical machine settings include; Plaque preheat temp=110° C., Shutter Close Temperature= 115° C., and Emitter temperature=600° C. When a Draw ratio X (X 100%)=and a Draw ratio Y (X 100%) 2 is performed on the as extruded film, the film modulus and elongation at break are both significantly improved over that found for the unstretched film.

Example 20

The material produced in Example 15, above, is injection molded into discs (thickness ⅛ inch, diameter 4 inches) and tensile bars. A Boy 30M (Boy Gmbh, Fernthalr, Germany) is used to injection mold the parts. The conditions used are as follows:

| | |
| --- | --- |
| Barrel temperature | 280° C. |
| Mold temperature | 50° C. |
| Screw speed | 210 rpm |
| Injection speed | 100% |
| Injection pressure | 13 bar |
| Hold pressure | 12 bar |
| Back pressure | 3 bar |
| Injection time | 2 seconds |
| Cooling time | 25 seconds |

Example 21

The polymer produced in Example 3, above, is used to produce a 14 mil thick sheet by extrusion using a film/sheet pilot line made by Egan Machinery (Somerville, N.J.). The conditions for extrusion are as follows:

| Extruder barrel temperatures | |
| --- | --- |
| Zone 1 | 255° C. |
| Zone 2 | 255° C. |

-continued

| Extruder barrel temperatures | |
| --- | --- |
| Zone 3 | 255° C. |
| Zone 4 | 255° C. |
| Zone 5 | 275° C. |
| Zone 6 | 275° C. |
| Melt line temp. | 50° C. |
| Die temp. | 280° C. |
| Roller 1 | 25° C. |
| Roller 2 | 25° C. |
| Roller 3 | 20° C. |

The sheet is trimmed to 6 to 7 inches wide and approximately 11 inches long. After heating in a rectangular retaining bracket at 165° C. in a convection oven until softening takes place, the sheet is vacuum thermoformed into 1½ inch and 2 inch deep room temperature molds to demonstrate ability to thermoform. The obtained containers are optically clear and mechanically robust.

Example 22

The polymers of the present invention produced in Examples 3 and 15, above, are made into 460 mL jars on a commercial Nissei ASB100DH Injection Single Blow stretch-blow molding unit using a one-stage stretch-blow molding process, and using a 132.5 mm rod for the stretch. The polymer is injection molded at a melt temperature of 275° C. to make a preform, which is then subjected to the stretch-blow molding process at 100° C. in the same equipment without complete cooling.

Example 23

The polymer of the present invention produced in Example 15, above, is ground and dried at 130° C. overnight in a vacuum. Rods are made from the polymer by first placing it in a mold which is then heated under gentle pressure from a plunger. The pressure is provided by a hydraulic press. When the polymer began to soften, more pressure (500–1000 lbs/in$^2$) is applied to compress the polymer into a hard rod. The ingress of moisture is reduced by encasing the equipment in a Lucite® box which is continuously purged by a flow of dry nitrogen.

Spinning is immediately carried out on a single filament spinning machine. The polymer is rod form is melted by pressing it against a heated "grid" which is conical in shape with a hole at the apex. The machine temperatures are slowly raised until the melted polymer starts to flow through this hole. In the present example, this occurs at approximately 270° C. The polymer is then filtered through a bed of 80/120 shattered metal, and finally emerges from the single hole spinneret capillary, 0.020 inch in diameter and 0.030 inch long. The throughput is 0.30 grams per minute (gpm), and the fiber, which is to be drawn, is taken up at 50 meters per minute (mpm). These condition are found to give low orientation single filaments of about 70 denier per filament (dpf). A temperature scan is made to produce the optimum spun fiber for subsequent drawing. A fiber sample is also made at the maximum take up speed possible in order to obtain a feel for the draw down and to measure the spun fiber properties.

Single filament drawing is performed on modular draw units with hot shoes between each roll. The fiber is drawn in two stages using the second stage to develop the maximum fiber tenacity and crystallinity. In this way, a single filament is collected and small samples cut from the last roll. A sample is tested for its thermal properties by the above-mentioned DSC method and for tensile properties using ASTM test method D3822. Its Tg is found by DSC to be above the Tg of a comparative polyester fiber without the isosorbide derivative.

What is claimed is:

1. Bis(2-hydroxyethyl)isosorbide.
2. A process for producing bis(2-hydroxyethyl)isosorbide comprising the steps of:
    (a) contacting isosorbide with a stoichiometric excess of ethylene carbonate in the presence of a catalyst,
    (b) heating the product of step (a) gradually, with mixing, at a temperature sufficient to substantially evolve carbon dioxide from said product, and
    (c) cooling the product of step (b) to ambient temperature.
3. The process of claim 2 wherein the temperature is from 50° C. to 300° C.
4. The process of claim 2 wherein the temperature is from 75° C. to 200° C.

* * * * *